United States Patent [19]

Müller et al.

[11] 4,126,630

[45] Nov. 21, 1978

[54] PROCESS FOR PREPARING OXIME CONTAINING SILICON COMPOUNDS

[75] Inventors: Horst Müller, Emmerting; Edgar Schmidt, Burghausen; Volker Frey, Burghausen; Rudolf Riedle, Burghausen, all of Germany

[73] Assignee: Wacker-Chemie GmbH, Munich, Germany

[21] Appl. No.: 887,168

[22] Filed: Mar. 16, 1978

[30] Foreign Application Priority Data

Apr. 28, 1977 [DE] Fed. Rep. of Germany ....... 2719008

[51] Int. Cl.$^2$ ................................................. C07F 7/10
[52] U.S. Cl. ........................ 260/448.2 E; 260/448.2 N
[58] Field of Search .................................. 260/448.2 E

[56] References Cited

U.S. PATENT DOCUMENTS

| | | | |
|---|---|---|---|
| 3,697,568 | 10/1972 | Boissieras et al. | 260/448.2 E X |
| 3,839,386 | 10/1974 | Lengnick | 260/448.2 E X |
| 4,033,991 | 7/1977 | Shinohara | 260/448.2 E |

Primary Examiner—Paul F. Shaver

[57] ABSTRACT

A process for preparing oxime containing silicon compounds which comprises reacting an oxime with a silicon compound having at least three nitrogen atoms linked to the same silicon atom through Si—N bonding per molecule.

5 Claims, No Drawings

PROCESS FOR PREPARING OXIME CONTAINING SILICON COMPOUNDS

The present invention relates to oxime containing silicon compounds and more particularily to a process for preparing oxime containing silicon compounds by reacting oximes with silicon compounds having at least three nitrogen atoms bonded to the same silicon atom through Si—N bonding per molecule.

BACKGROUND OF THE INVENTION

Heretofore oxime containing silicon compounds have been prepared by reacting silicon compounds having Si-halogen bonds with oximes, preferably in the presence of acid acceptors, such as triethylamine, pyridine, alpha-picoline or mixtures thereof. (See U.S. Pat. No. 3,674,738.)

In comparison to the process described in the above cited patent, the process of this invention has certain advantages. For example, the reaction proceeds at a rapid rate and excellent yields of desired product are obtained in the absence of expensive acid acceptors.

Therefore, it is an object of this invention to provide a process for preparing oxime containing silicon compounds. Another object of this invention is to provide a process for preparing oxime containing silicon compounds in the absence of acid acceptors. A further object of this invention is to provide a process for preparing oxime containing silicon compounds by reacting oximes with silicon compounds having at least three nitrogen atoms bonded to the same silicon atom through Si—N bonding per molecule.

SUMMARY OF THE INVENTION

The foregoing objects and others which will become apparent from the following description are accomplished in accordance with this invention, generally speaking, by providing a process for preparing oxime containing silicone compounds which comrises reacting oximes with silicon compounds having at least three nitrogen atoms linked to the same silicon atom through Si—N bonding per molecule at a temperature of from about 0° C. up to about 150° C.

DETAILED DESCRIPTION OF INVENTION

Oximes which have been employed heretofore in the reaction with silicon compounds having Si-bonded halogen atoms, especially Si-bonded chlorine atoms, may be used in the process of this invention. These oximes can be represented by the general formula:

HON=X in which X is =CRR$^1$ or =CR$^2$, R represents a monovalent or a substituted monovalent hydrocarbon radical, R$^1$ is hydrogen or the same as R and R$^2$ represents a bivalent or a substituted bivalent hydrocarbon radical.

Examples of hydrocarbon radicals represented by R and R$^1$ are alkyl radicals, such as the methyl, ethyl, n-propyl, isopropyl, n-butyl and sec-butyl radical as well as octadecyl radicals; alkenyl radicals, such as the vinyl and allyl radical; saturated cyclo-aliphatic hydrocarbon radicals such as the cyclopentyl and cyclohexyl radical, as well as methylcylohexyl radicals; cycloaliphatic hydrocarbon radicals having carbon-carbon multiple bonds, such as the cyclohexenyl radical; aryl radicals such as the phenyl radical, as well as the xenyl and naphthyl radicals; aralkyl radicals such as the benzyl, beta-phenylethyl and beta-phenylpropyl radical and alkaryl radicals such as the tolyl radicals.

Examples of preferred substituted hydrocarbon radicals represented by R and R$^1$ are perfluoralkylethyl radicals such as the 3,3,3-trifluoropropyl radicals and haloaryl radicals such as chlorophenyl radicals and cyanoalkyl radicals such as the beta-cyanoethyl radicals.

Examples of R$^2$ radicals, i.e. bivalent, or substituted bivalent hydrocarbon radicals which form a ring with the carbon atom of the C=ON group, are those of the following formulas:

—CH$_2$(CH$_2$)$_3$CH$_2$—

—CH$_2$(CH$_2$)$_4$CH$_2$—

—C$_6$H$_4$C$_6$H$_4$—

—CH$_2$[C(CH$_3$)$_2$]CH$_2$CH$_2$—

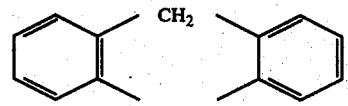

and hydrocarbon radicals which are substituted by halogen, namely those having the following formulas:

—CH$_2$CHCl(CH$_2$)$_3$—

—C$_6$H$_4$C$_6$H$_3$Br—

—CF$_2$(CF$_2$)$_3$CF$_2$—

—CH$_2$CH$_2$[C(CCl$_3$)$_2$]CH$_2$—.

Mixtures of various oximes may also be employed.

The silicon compounds used in accordance with this invention in which at least three Si—N bonds are bonded to the same silicon atom, may contain one or more silicon atoms per molecule. Silicon compounds having a silicon atom with at least three nitrogen atoms bonded thereto are preferably those of the formula:

R$_a$Si(NR$_2^1$)$_{4-a}$, where R and R$^1$ are the same as above and $a$ is zero or 1.

It is preferred that the silicon compounds which contain more than one silicon atom per molecule and have at least three nitrogen atoms linked to one silicon atom through Si—N bonding, have from 2 to 22 silicon atoms per molecule. Moreover, it is preferred that the silicon compounds which contain more than one silicon atom per molecule and have three nitrogen atoms bonded to one silicon atom through Si—N bonding, that the silicon valences which are satisfied by substituents other than nitrogen and monovalent or substituted monovalent hydrocarbon radicals, be saturated with siloxane-oxygen atoms or bivalent hydrocarbon radicals.

The following formulas represent silicon compounds containing more than one silicon atom per molecule in which at least three nitrogen atoms are bonded to the same silicon atom through Si—N bonding:

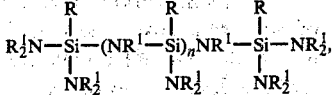

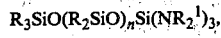

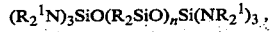

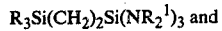

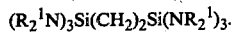

In the above formulas, R and $R^1$ are the same as defined above and $n$ is zero or represents an integer of from 1 to 20.

Examples of substituted and unsubstituted hydrocarbon radicals represented by R and $R^1$ in the oximes are, with the exception of the vinyl radical in the case of nitrogen bonded R and $R^1$ radicals, equally applicable to the substituted and unsubstituted hydrocarbon radicals represented by R and $R^1$ in the above represented formulas for silicon compounds having at least three nitrogen atoms linked to the same silicon atom through Si—N bonding. Additional examples of nitrogen bonded radicals R and $R^1$ are the tert-butyl radical, the 3,5,5-trimethylcyclohexyl radical and the 2,3,4-triethylcyclohexyl radical.

Mixtures of various silicon compounds may be employed as well.

It is now possible with the process of this invention to prepare silicon compounds in which only a portion of the original Si—N bonds is substituted by SiON=C bonds, by using less than one mol of oxime for each gram-atom of Si-bonded nitrogen. However it is also possible to prepare silicon compounds in which all of the original Si—N bonds are replaced by SiON=C bonds, by reacting at least one mol and preferably 1 to 2 mols of oxime per gram-atom of Si-bonded nitrogen. Thus, the process of this invention now makes it possible to prepare silicon compounds having oxime groups which are bonded to silicon via oxygen, in accordance with the following formula:

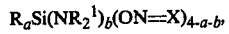

where R, $R^1$ X and $a$ are the same as above, $b$ is zero, 1, 2 or 3, with the provisio that the sum of $a + b$ can be no greater than 3, when silicon compounds having the following general formula are

The process of this invention is preferably carried out at temperatures of from 0° to 150° C. and more preferably from 15° to about 50° C. Also, it is preferred that the process be conducted at atmospheric pressure, i.e., at 760 mm Hg (abs.) or approximately 760 mm Hg (abs.). However is desired, the process may be conducted either at lower or higher pressures.

It is preferred that the process be performed under anhydrous conditions; however the exculsion of water is not essential where the formation of oligomer products does not cause any problems.

One of the advantages of the process of this invention is that the use of inert solvents is not essential; however, they may be used if desired. Examples of suitable inert solvents which may be used in this process are hydrocarbons such as petroleum ether, benzene and toluene; esters such as ethyl acetate; ethers such as diethyl ether, di-n-butyl ether, dioxane and tetrahydrofuran; ketones such as acetone; chlorinated hydrocarbons such as methylene chloride; as well as hexamethyldisiloxane.

The process may be conducted batchwise, continuously or semi-continuously.

The excess oxime as well as the ammonia or the amine formed during the reaction of the oxime with a silicon-bonded group of the formula $NR_2^1$ can easily be removed by distillation at atmospheric or below atmospheric pressure, so that a pure product can be easily obtained.

The silicon compounds having oxime groups bonded to silicon via oxygen which are obtained from the process of this invention may be used as cross-linking agents in the preparation of compositions which can be stored under anhydrous conditions, but cure to elastomers when exposed to water at room temperature. These curable compositions are prepared by mixing diorganopolysiloxanes containing condensable terminal groups with the oxime containing cross-linking agents of this invention.

EXAMPLES 1 through 10

In each of the following examples one mol of silane is mixed with the oxime and the mixture so obtained is stirred for 3 hours at 30° C. under anhydrous conditions. Subsequently the volatile components of the reaction mixture are distilled off at 10 to 20 mm Hg (abs.) and at a bath temperature of from 100° to 120° C. The distillation residue has the formula and the physical properties indicated in the Table. The formulas representing the silane products obtained from the reaction are represented as average values. The yield is based on the silane used in the reaction. In the formulas "$C_6H_{11}$" refers to the cyclohexyl radical.

EXAMPLE 11

(a) In order to determine the reaction speed, methyltris-(cyclohexylamino)-silane is mixed in a Nuclear Magnetic Resonance tube with methyl-ethylketoxime at a ratio of 1 mol of silane to 4 mols of oxime. After 5 minutes all NMR aminosilane signals have disappeared and only the methyl proton signal from the pure methyltris-(methyl-ethylketoxime)silane can be detected. It is thus a very quick and quantitative reaction.

(b) In order to determine the location of the equilibrium in the reaction pursuant to this invention:

methyltris-(methylethylketoxime)-silane is mixed with cyclohexylamine in the ratio of one mol of silane to two mols of amine and heated to 60° C. After 7 days of heating at 60° C., gas chromatographic analysis does not reveal that any aminosilane or aminoximosilane have formed. It thus appears that the equilibrium is located entirely on the right hand side of the above reaction equation, so that it is not necessary to remove the amine or ammonia during the reaction.

TABLE

| Example No. | Silane | Oxime | Oxime Mol | Product | Yield % | Physical Properties |
|---|---|---|---|---|---|---|
| 1 | $CH_3Si(NHC_6H_{11})_3$ | $HON=C(CH_3)C_2H_5$ | 1.5 | $CH_3Si(NHC_6H_{11})_{1.5}[ON=C(CH_3)C_2H_5]_{1.5}$ | 99 | $n_D^{25}=1.4687$ |
| 2 | $CH_3Si(NHC_6H_{11})_3$ | $HON=C(CH_3)C_2H_5$ | 4 | $CH_3Si[ON=C(CH_3)C_2H_5]_3$ | 95 | $n_D^{25}=1.436$ |
| 3 | $CH_3Si(NHC_6H_{11})_3$ | $HON=C(CH_3)_2$ | 2 | $CH_3SiNHC_6H_{11}[ON=C(CH_3)_2]_2$ | 98 | $n_D^{25}=1.4661$ |
| 4 | $CH_3Si(NHC_6H_{11})_3$ | $HON=C(CH_3)_2$ | 3.5 | $CH_3Si[ON=C(CH_3)_2]_3$ | 96 | $n_D^{25}=1.4568$ |
| 5 | $CH_3Si(NHsec-C_4H_9)_3$ | $HON=C(CH_3)C_2H_5$ | 2 | $CH_3SiNHsec-C_4H_9[ON=C(CH_3)C_2H_5]_2$ | 98 | $n_D^{25}=1.4460$ |
| 6 | $C_6H_5Si(NHC_6H_{11})_3$ | $HON=C(CH_3)C_2H_5$ | 1.5 | $C_6H_5Si(NHC_6H_{11})_{1.5}[ON=C(CH_3)C_2H_5]_{1.5}$ | 99 | $n_D^{25}=1.5119$ |
| 7 | $C_6H_5Si(NHC_6H_{11})_3$ | $HON=C(CH_3)C_2H_5$ | 4 | $C_6H_5Si[ON=C(CH_3)C_2H_5]_3$ | 99 | $n_D^{25}=1.5016$ |
| 8 | $C_2H_3Si(NHC_6H_{11})_3$ | $HON=C(CH_3)C_2H_5$ | 1.5 | $C_2H_3Si(NHC_6H_{11})_{1.5}[ON=C(CH_3)C_2H_5]_{1.5}$ | 94 | $n_D^{25}=1.4772$ |
| 9 | $C_2H_3Si(NHC_6H_{11})_3$ | $HON=C(CH_3)C_2H_5$ | 4 | $C_2H_3Si[ON=C(CH_3)C_2H_5]_3$ | 96 | $n_D^{25}=1.4649$ |
| 10 | $Si(NHsec-C_4H_9)_4$ | $HON=C(CH_3)C_2H_5$ | 5 | $Si[ON=C(CH_3)C_2H_5]_4$ | 99 | Fp. $=65°$ C |

What is claimed is:

1. A process for preparing oxime containing silicon compounds which comprises reacting an oxime with a silicon compound having at least three nitrogen atoms linked to the same silicon atom of said compound through Si—N bonding at a temperature of from about 0° to 150° C.

2. The process of claim 1, wherein the oxime is reacted with the silicon compound in a ratio of one mol of oxime for each gram atom of Si-bonded nitrogen.

3. The process of claim 1, wherein the reaction is conducted at a temperature of from 15° to 50° C.

4. The process of claim 1, wherein the oxime has the formula

HON=X, in which X is selected from the group consisting of $CRR^1$ and $CR^2$, R is selected from the group consisting of monovalent hydrocarbon radicals and substituted monovalent hydrocarbon radicals, $R^1$ is selected from the group consisting of hydrogen and R, and $R^2$ is selected from the group consisting of bivalent hydrocarbon radicals and substituted bivalent hydrocarbon radicals.

5. The process of claim 1, wherein the silicon compound has the formula $R_aSi(NR_2^1)_{4-a}$, in which R is selected from the group consisting of monovalent hydrocarbon radicals and substituted monovalent hydrocarbon radicals, $R^1$ is selected from the group consisting of hydrogen and R and a is 0 or 1.

* * * * *